(12) United States Patent
Thompson et al.

(10) Patent No.: US 8,574,829 B2
(45) Date of Patent: Nov. 5, 2013

(54) METHODS OF TREATING CANCER WITH PHENFORMIN

(75) Inventors: Craig B. Thompson, Merion Station, PA (US); Roland Knoblauch, Wynnewood, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/260,838

(22) PCT Filed: Mar. 30, 2010

(86) PCT No.: PCT/US2010/029112
§ 371 (c)(1),
(2), (4) Date: Jan. 3, 2012

(87) PCT Pub. No.: WO2010/114805
PCT Pub. Date: Oct. 7, 2010

(65) Prior Publication Data
US 2012/0114676 A1    May 10, 2012

Related U.S. Application Data

(60) Provisional application No. 61/165,186, filed on Mar. 31, 2009.

(51) Int. Cl.
*C12Q 1/00* (2006.01)
*A01N 37/52* (2006.01)

(52) U.S. Cl.
USPC .............................................. 435/4; 514/635

(58) Field of Classification Search
None
See application file for complete search history.

(56) References Cited

U.S. PATENT DOCUMENTS 6,797,729 B1    9/2004   Byrne et al.
2008/0153877 A1*   6/2008   Adimoolam et al. ......... 514/320

OTHER PUBLICATIONS

Gleason et al (JBC, 2007, 282(14): 10341-10351).*
Bi et al., "CCR: a rapid and simple approach for mutation detection," Nucleic Acids Res., Jul. 15, 1997, 25(14), 2949-2951.
Caraci, et al., "Effects of phenformin on the proliferation of human tumor cell lines," Life Sciences, Dec. 19, 2003, 74(5), 643-650.
De Galitiis et al., "Novel P53 mutations detected by FAMA in colorectal cancers," Ann. Oncol., Jun. 2006, 17(Suppl. 7), vii78-vii83.
Dilman et al., "Potentiation of antitumor effect of cyclophosphamide and hydrazine sulfate by treatment with the antidiabetic agent, 1-phenylethylbiguanide (phenformin)," Cancer Lett., Oct. 1979, 7(6), 357-361.
Ekstrøm et al., "Detection of low-frequency mutations in exon 8 of the TP53 gene by constant denaturant capillary electrophoresis (CDCE)," Biotechniques, Jul. 1999, 27(1), 128-134.
Gelfi et al., "Detection of p53 point mutations by double-gradient, denaturing gradient gel electrophoresis," Electrophoresis, Dec. 1997, 18(15), 2921-2927.
Gross et al., "Mutation analysis of p53 in ovarian tumors by DHPLC," J. Biochem. Biophys. Methods, Jan. 30, 2001, 47(1-2), 73-81.
Hakkarainen et al., "TP53 mutation detection by SSCP and sequencing," Methods Mol. Med., 2004, 97, 191-208.
Harrison et al., "Impact of tumor hypoxia and anemia on radiation therapy outcomes," Oncologist, Dec. 2002, 7(6), 492-508.
Inganäs et al., "Enzymatic mutation detection in the P53 gene," Clin. Chern., Oct. 2000, 46(10), 1562-1573.
Ishioka et al., "Screening patients for heterozygous p53 mutations using a functional assay in yeast," Nat. Genet., Oct. 1993, 5(2), 124-129.
International Patent Application No. PCT/US2010/029112: International Search Report and Written Opinion dated Jun. 3, 2010, 6 pages.
Schumacker et al., "Oxygen conformance of cellular respiration in hepatocytes," Am. J. Physiol., Oct. 1993, 265(4 Pt.1), L395-L402.
Semenza, G. L., "Targeting HIF-1 for cancer therapy," Nat. Rev. Cancer, Oct. 2003, 3(10), 721-732.
Takahashi et al., "Clinical application of oligonucleotide probe array for full-length gene sequencing of TP53 in colon cancer," Oncology, 2003, 64(1), 54-60.
Tomiyama et al., "Critical role for mitochondrial oxidative phosphorylation in the activation of tumor suppressors Bax and Bak," J. Natl. Cancer Inst., Oct. 18, 2006, 98(20), 1462-1473.
Tsongalis et al., "Rapid screening for p53 mutations with a sensitive heteroduplex detection technique," Clin. Chem., Mar. 1994, 40(3), 485-486.
Wilson et al., "A novel optical biosensor format for the detection of clinically relevant TP53 mutations," Biosens. Bioelectron., May 15, 2005, 20(11), 2310-2313.

* cited by examiner

*Primary Examiner* — Sean Aeder
(74) *Attorney, Agent, or Firm* — Woodcock Washburn, LLP

(57) ABSTRACT

Methods of using phenformin to treat certain types of cancers are described.

16 Claims, 11 Drawing Sheets

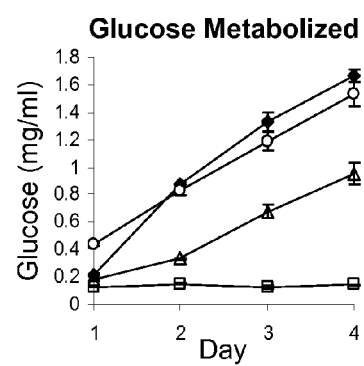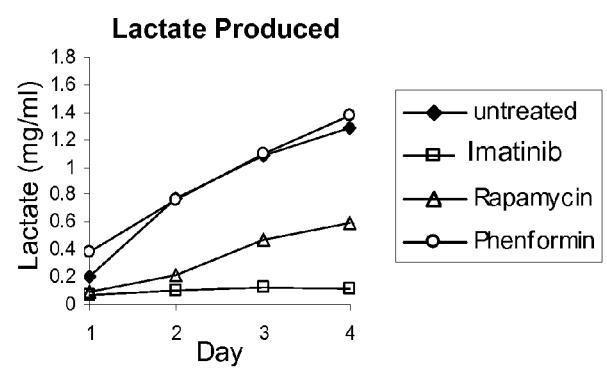
FIG. 5A                     FIG. 5B

METHODS OF TREATING CANCER WITH PHENFORMIN

CROSS-REFERENCE TO RELATED APPLICATIONS

This application is the National Stage of International Application No. PCT/US2010/029112, filed Mar. 30, 2010, which claims the benefit of U.S. Provisional Application No. 61/165,186, filed Mar. 31, 2009, the disclosures of which are incorporated herein by reference in their entireties.

TECHNICAL FIELD

The invention relates to the treatment of certain types of cancer with a biguanide such as phenformin as well as related methods, compounds and compositions.

BACKGROUND

Phenformin is a biguanide compound that has been used to treat diabetes, in particular, type 2 diabetes.

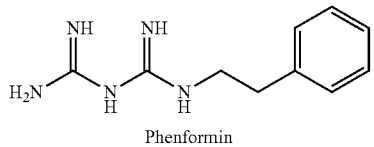 [SMILES: N=C(N)NC(=N)NCCc1ccccc1]

Phenformin

Despite its efficacy as a hypoglycemic agent, phenformin is no longer available for the treatment of diabetes in the United States due to its association with an increased risk of lactic acidosis. Metformin, another biguanide, has replaced phenformin in the United States for the treatment of diabetes.

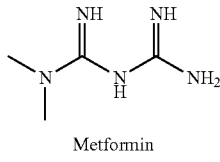

Metformin

The incidence of lactic acidosis associated with metformin is significantly less than that observed with phenformin.

Recent studies have indicated that phenformin may have antitumor activity. See Filippo Caraci, et al., "Effects of phenformin on the proliferation of human tumor cell lines," *Life Sciences*, 2003 Dec. 19:74 (5):643-50; Dilman and Anisimov, "Potentiation of antitumor effect of cyclphosphamide and hydrazine sulfate by treatment with the antibiabetic agent, 1-phenylethylbiguanide (phenformin)," *Cancer Lett.* 1979 October; 7 (6):357-61. The mechanisms of how phenformin affects tumor growth must be elucidated in order to maximize the potential for success in using phenformin to treat cancer. Thus, there remains a need to identify whether phenformin will likely be effective in suppressing growth of particular tumor-types.

It is well known in the art that oxygen is a potent radiosensitizer that can increase the effectiveness of a dose of radiation by, for example, forming free radicals that can damage DNA. One of the limitations of radiation therapy used to treat cancer is that the cells of solid tumors become deficient in oxygen after exposure to radiation, resulting in a hypoxic environment. Tumor cells in a hypoxic environment can be 2 to 3 times more resistant to radiation damage than those in a normal oxygen environment. Harrison L. B., et al. *Impact of tumor hypoxia and anemia on radiation therapy outcomes*, Oncologist 7 (6):492-508. Thus, there remains a need to identify compounds that can sensitize cancer cells to radiation therapy.

SUMMARY

Methods of treating cancer in a patient using phenformin are described. In particular, the methods comprise assaying the cancer for at least one of p53 deficiency, over-expression of c-myc, Bax-deficiency, Bak-deficiency, and glutamine dependence; and in response to a positive assay for at least one of p53 deficiency, over-expression of c-myc, Bax-deficiency, Bak deficiency, and glutamine dependence, administering to the patient a therapeutically effective amount of phenformin. Methods for adjusting the chemotherapeutical treatment of a neoplasm are also described. The invention is also directed to methods of radiosensitizing cancer cells by administering phenformin.

BRIEF DESCRIPTION OF THE DRAWINGS

FIG. 5A depicts the effects of imatinib, rapamycin, and phenformin on glucose metabolism.

FIG. 5B depicts the effects of imatinib, rapamycin, and phenformin on lactate production.

DETAILED DESCRIPTION OF ILLUSTRATIVE EMBODIMENTS

Figure 1A:
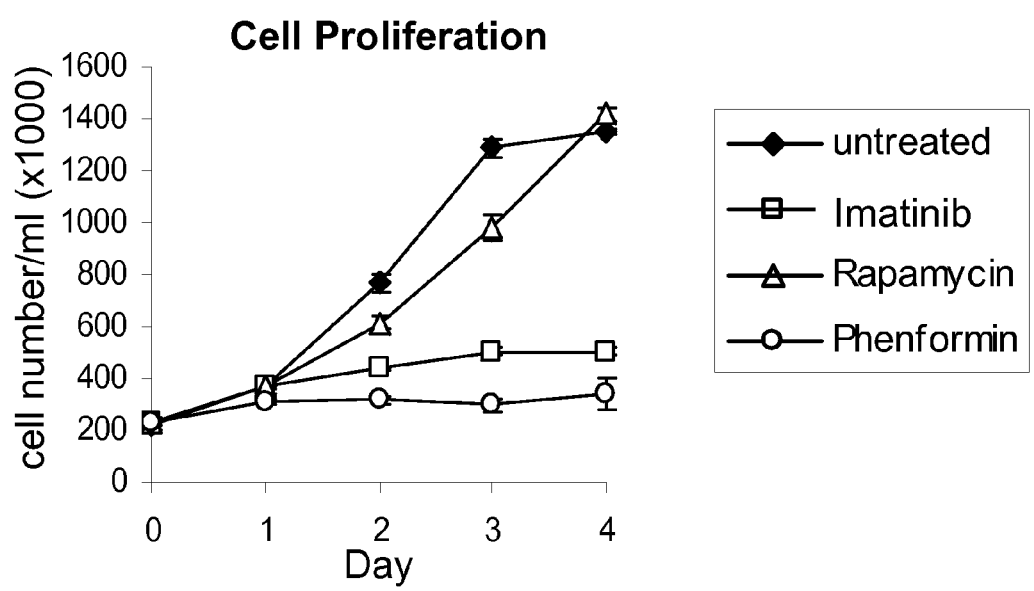
FIG. 1A depicts the effect of imatinib, rapamycin, and phenformin on the proliferation of chronic myelogenous leukemia (CML) cells (K562 cells).

The methods described herein include methods of administering phenformin to a subject wherein the subject has a cancer characterized as described herein. In some embodiments, the cancer is characterized as deficient in p53. In some embodiments, the cancer is characterized as having over-expression of c-myc. In some embodiments, the cancer is characterized as having unwanted mitochondrial electron transport chain activity (e.g., unwanted oxygen consumption and/or unwanted levels of ATP). In some embodiments, the cancer is characterized as glutamine-dependent. In some embodiments, the cancer is characterized as being deficient in Bax or Bak.

As used herein, deficient in p53 or p53$^{-/-}$, means that sufficient cells of the tumor lack one or both functional copies of the p53 gene such that there is an effect on the growth of the tumor. In certain embodiments at least 2, 5, 10, 20, 30, 40, or 50 of the cells in a tumor sample have less than two functional copies of p53.

As used herein, "c-myc" refers to an oncogene that is a member of the helix-loop-helix/leucine-zipper superfamily. C-myc is overexpressed in certain cancers.

As used herein, "mitochondrial electron transport chain activity" refers to the activity of the chemical reactions between an electron donor (such as NADH) and an electron acceptor (such as O$_2$) to the transfer of H$^+$ ions across the mitochondrial membrane.

As used herein, "glutamine metabolism" refers to the uptake and use of glutamine in a cell such as a cancer cell.

As used herein "Bax" and "Bak" refers to proteins in the Bcl-2 gene family. In some instances, Bax or Bak promotes apoptosis, for example, by competing with Bcl-2. Certain cancers exhibit a deficiency in BAX and/or Bak.

As used herein, the terms "cancer" and "neoplasm" are meant to include all types of cancerous growths or oncogenic processes, metastatic tissues or malignantly transformed cells, tissues, or organs, irrespective of histopathologic type or stage of invasiveness. Cancers amenable to treatment using the methods described herein will be those cancers that assay positively for at least one of a deficiency in p53, over-expression of c-myc, Bax deficiency, or Bak deficiency. Clinicians will be readily able to ascertain whether one of more of these characteristics is present in a tumor sample using methods known in the art, in combination with the present disclosure.

As used herein, "treatment of cancer" includes, e.g., slowing, eliminating, or reversing tumor growth, reducing, either in number or size, metastases, reducing or eliminating tumor cell invasiveness, providing an increased interval to tumor progression, or increasing disease-free survival time. In preferred embodiments of the invention, the cancer is leukemia, in particular, chronic myelogenous leukemia cells.

A "therapeutically effective amount" refers to an amount which, when administered in a proper dosing regimen, is sufficient to reduce or ameliorate the severity, duration, or progression of the disorder being treated (e.g., cancer), prevent the advancement of the disorder being treated (e.g., cancer), cause the regression of the disorder being treated (e.g., cancer), or enhance or improve the prophylactic or therapeutic effects(s) of another therapy. An effective amount of the compound described above may range from about 0.1 mg/Kg to about 500 mg/Kg, alternatively from about 1 to about 50 mg/Kg. Effective doses will also vary depending on route of administration, as well as the possibility of co-usage with other agents. Clinicians can readily determine the therapeutically effective amount using techniques known in the art.

The methods described herein include administering phenformin to a subject wherein the subject has a cancer deficient in p53 (e.g., a p53$^{-/-}$ cancer (e.g., a p53$^{-/-}$ tumor)). A cancer can be evaluated to determine whether it is p53$^{-/-}$ using various methods known in the art. Accordingly, described herein are methods of selecting a patient to be treated with phenformin. The method includes evaluating the patient to determine if the patient is suffering from a cancer deficient in p53. This can be readily accomplished by evaluating a biopsy sample of the patient's cancer and/or tumor(s). If it is determined that the patient is suffering from a cancer deficient in p53, the clinician then treats or instructs to treat the patient with phenformin.

Exemplary methods for evaluating a cancer to determine whether the cancer is p53$^{-/-}$ include, for example, evaluating a subject for a p53 mutation, for example, by direct DNA sequencing or Immunohistochemistry (IHC). Other exemplary methods for evaluating a subject for p53 deficiency include, for example, Single-stranded conformation polymorphism (SSCP), for example, as described in Hakkarainen J et al. TP53 mutation detection by SSCP and sequencing. Methods Mol Med. 2004; 97:191-208; Denaturing gradient gel eletrophoresis (DGGE), for example, as described in Gelfi C et al., Detection of p53 point mutations by double-gradient, denaturing gradient gel electrophoresis. Electrophoresis. 1997 December; 18 (15):2921-7; Fluorescence-assisted mismatch analysis (FAMA), for example, as described in De Galitiis F et al., Novel P53 mutations detected by FAMA in colorectal cancers. Ann Oncol: 2006 June; 17 Suppl 7:vii78-83; Denaturing high-performance liquid chromatography (DHPLC), for example, as described in Gross E et al. Mutation analysis of p53 in ovarian tumors by DHPLC. J Biochem Biophys Methods. 2001 Jan. 30; 47 (1-2):73-81; Enzymatic mutation detection (EMD), for example, as described in Inganäs M et al., Enzymatic mutation detection in the P53 gene. Clin Chem. 2000 October; 46 (10):1562-73; Constant denaturant capillary electrophoresis (CDCE), for example, as described in Ekstrøm P O et al., Detection of low-frequency mutations in exon 8 of the TP53 gene by constant denaturant capillary electrophoresis (CDCE). Biotechniques. 1999 July; 27 (1):128-34; Heteroduplex detection, for example, as described in Tsongalis G J et al., Rapid screening for p53 mutations with a sensitive heteroduplex detection technique. Clin Chem. 1994 March; 40 (3):485-6; Functional analysis of separated alleles in yeast (FASAY), for example, as described in Ishioka C et al., Screening patients for heterozygous p53 mutations using a functional assay in yeast. Nat. Genet. 1993 October; 5 (2):124-9; Combined Chain Reaction (CCR), for example, as described in Bi W and Stambrook P J, CCR: a rapid and simple approach for mutation detection. Nucleic Acids Res. 1997 Jul. 15; 25 (14):2949-51; Oligonucleotide array/DNA chip, for example, as described in Takahashi Y et al. Clinical application of oligonucleotide probe array for full-length gene sequencing of TP53 in colon cancer. Oncology. 2003; 64 (1):54-60; and Biosensors e.g., Surface plasmon resonance (SPR), for example, as described in Wilson P K et al., A novel optical biosensor format for the detection of clinically relevant TP53 mutations. Biosens Bioelectron. 2005 May 15; 20 (11):2310-3.

The methods described herein include administering phenformin to a patient wherein the patient has a cancer that over-expresses c-myc. A cancer can be evaluated to determine whether it over-expresses c-myc by using various methods known in the art. Accordingly, described herein are methods of selecting a patient to be treated with phenformin. The method includes evaluating a patient to determine if the patient is suffering from a cancer having an overexpression of c-myc, and if the patient is suffering from a cancer having an over-expression of c-myc, then treating or instructing to treat the subject with phenformin.

The methods described herein include administering phenformin to a patient wherein the patient has a cancer having unwanted mitochondrial electron transport chain activity (e.g., unwanted in oxygen consumption and/or unwanted levels of ATP). A cancer can be evaluated to determine whether it has unwanted mitochondrial electron transport chain activity (e.g., unwanted oxygen consumption and/or unwanted levels of ATP) using various methods known in the art. Accordingly, described herein are methods of selecting a subject (or patient) to be treated with phenformin. The method includes evaluating a patient to determine if the patient is suffering from a cancer having unwanted mitochondrial electron transport chain activity (e.g., a decrease in oxygen consumption and/or a decrease in level of ATP), and if the patient is suffering from a cancer having unwanted mitochondrial electron transport chain activity (e.g., unwanted oxygen consumption and/or unwanted levels of ATP) then treating or instructing to treat the patient with phenformin.

The methods described herein include administering phenformin to a subject wherein the subject has a cancer that it glutamine dependent. A cancer can be evaluated to determine whether it is glutamine dependent using various methods known in the art. Accordingly, described herein are methods of selecting a patient to be treated with a phenformin. The method includes evaluating a patient to determine if the patient is suffering from a cancer that is glutamine dependent and if the patient is suffering from a cancer that is glutamine dependent, then treating or instructing to treat the subject with phenformin.

The methods described herein include administering phenformin to a subject wherein the subject has a cancer deficient in Bax and/or Bak (e.g., characterized as being deficient in Bax and/or Bak). A cancer can be evaluated to determine whether it is deficient in Bax and/or Bak (e.g., characterized as being deficient in Bax and/or Bak) using various methods known in the art. Accordingly, described herein are methods of selecting a patient to be treated with phenformin. The method includes evaluating a patient to determine if the patient is suffering from a cancer deficient in Bax and/or Bak (e.g., characterized as being deficient in Bax and/or Bak), and if the patient is suffering from a cancer deficient in Bax and/or Bak (e.g., characterized as being deficient in Bax and/or Bak) then treating or instructing to treat the patient with phenformin.

It is known in the art that hypoxia-inducible factor 1 (HIF-1) activates transcription genes involved in, for example, tumor growth and tumor angiogenesis. Gregg L. Semenza, *Targeting HIF-1 for Cancer Therapy*, Nat. Rev. Cancer. 2003 October; 3 (10):721-32. Manipulation of HIF-1, either by genetic or pharmacological means, has demonstrated effects on tumor growth in xenograft assays. Id. at 728. It has been discovered that phenformin prevents hypoxia and HIF-1 induction. See FIG. 10. As such, the present invention is also directed to methods of treating cancer in a patient comprising administering to the patient a therapeutically effective amount of phenformin. Preferred embodiments are directed to methods of decreasing the rate of tumor growth in a patient comprising administering to the patient a therapeutically effective amount of phenformin. Other preferred embodiments are directed to methods of decreasing tumor angiogenesis in a patient comprising administering to the patient a therapeutically effective amount of phenformin.

Other preferred methods of the invention are directed to radiosensitizing cancer cells in a patient. As demonstrated in FIG. 10(A), K562 cells that were treated with phenformin maintained an oxygen-rich environment, as compared to untreated K562 cells. An oxygen rich environment is known in the art to increase the effectiveness of a dose of radiation by creating free radicals. As phenformin-treated cells consume less oxygen than untreated cells, a more oxygen-rich environment is created in the samples treated with phenformin. These phenformin-treated cells will likely be more susceptible to radiation-induced DNA-damage as compared to an untreated sample. As such, in certain embodiments, the invention is directed to methods of increasing the efficacy of radiation in treating cancer in a patient comprising administering phenformin to the patient and administering radiation to the cancer.

Disorders

The disclosed methods are useful in the prevention and treatment of solid tumors, soft tissue tumors, and metastases thereof wherein the solid tumor, soft tissue tumor or metastases thereof is a cancer described herein (e.g., a p53 deficient cancer, a having unwanted expression of c-myc (e.g., a cancer characterized by overexpression of c-myc), cancer having unwanted mitochondrial electron transport chain activity (e.g., a cancer characterized as in need of a decrease in oxygen consumption and/or a decrease in level of ATP), a cancer characterized by glutamine-dependency, or a cancer deficient in Bax or Bak (e.g., a cancer characterized as being deficient in Bax or Bak).

The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

The methods described herein can be administered with any cancer having the characteristic described herein, for example those described by the national cancer institute. A cancer can be evaluated to determine whether it is using a method described herein. Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood'; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Combination Therapies

In some embodiments, phenformin, is administered together with an additional cancer treatment. Exemplary cancer treatments include, for example, chemotherapy, targeted therapies such as antibody therapies, immunotherapy, and hormonal therapy. Examples of each of these treatments are provided below.

Chemotherapy

In some embodiments, phenformin is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase. Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU). Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin. Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein, e.g., a biguanide such as metformin or phenformin, preferably phenformin.

Targeted Therapy

In some embodiments, a compound described herein, e.g., a biguanide such as metformin or phenformin, preferably phenformin, is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib (GLEEVEC®), gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Ctuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, phenformin is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein, e.g., a biguanide such as metformin or phenformin, preferably phenformin.

Hormonal Therapy

In some embodiments, phenformin is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein, e.g., a biguanide such as metformin or phenformin, preferably phenformin.

Compositions and Routes of Administration

The compositions delineated herein include phenformin, as well as additional therapeutic agents, if present, in amounts effective for achieving a modulation of disease or disease symptoms, including those described herein.

The term "pharmaceutically acceptable excipient" refers to a carrier or adjuvant that may be administered to a patient, together with a compound of this invention, and which does not destroy the pharmacological activity thereof and is non-toxic when administered in doses sufficient to deliver a therapeutic amount of the compound.

Pharmaceutically acceptable carriers, diluents, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, sterile aqueous solutions, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, diluents, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Kits

A compound described herein described herein can be provided in a kit. The kit includes (a) a composition that includes phenformin and, optionally, (b) informational material. The informational material can be descriptive, instructional, marketing or other material that relates to the methods described herein and/or the use of a compound described herein for the methods described herein.

In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound described herein in a suitable manner to perform the methods described herein, e.g., in a suitable dose, dosage form, or mode of administration (e.g., a dose, dosage form, or mode of administration described herein). In another embodiment, the informational material can include instructions to administer a compound described herein to a suitable subject, e.g., a human, e.g., a human having or at risk for a disorder described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

It has been discovered that phenformin can be used to treat certain types of cancer, for example a cancer that is characterized by $p53^{-/-}$ cells. A biguanide such as phenformin or metformin (preferably phenformin) can also be used to treat cancer a cancer characterized by unwanted expression of c-myc such as BCR-Abl induced c-myc expression, a cancer having unwanted mitochondrial electron transport chain activity (e.g., a cancer characterized as having unwanted in oxygen consumption and/or unwanted levels of ATP), a cancer characterized as having unwanted glutamine metabolism (e.g., unimpaired glutamine metabolism), or a cancer characterized as deficient in Bax or Bak.

In one aspect, the method features a method of treating a patient suffering from a cancer characterized by cells that are deficient in p53 including the step of administering to the patient in need thereof a pharmaceutical composition comprising phenformin and a pharmaceutically acceptable carrier.

In some embodiments, the method includes the additional step of assaying the cancer for p53 deficiency prior to the administration of phenformin. In some embodiments, the method includes the additional step of evaluating the patient for a p53 mutation, for example, by direct DNA sequencing or Immunohistochemistry (IHC). In some embodiments, the cancer is selected from colon cancer or leukemia. In some embodiments, the cancer is characterized by unwanted expression of c-myc (e.g., prior to the administration of phenformin). In some embodiments, the cancer is characterized by unwanted consumption of oxygen or unwanted levels of ATP (e.g., prior to the administration of phenformin). In some embodiments, the cancer is characterized by unwanted mitochondrial electron transport activity (e.g., prior to the administration of phenformin). In some embodiments, the cancer is characterized by unwanted glutamine metabolism (e.g., prior to the administration of phenformin). In some embodiments, the cancer is characterized by Bax or Bak deficiency (e.g., prior to the administration of phenformin).

In some embodiments, the method includes the additional step of subjecting the patient in need thereof to a second anti-cancer therapeutic treatment selected from radiation therapy, chemotherapy or treatment with a targeted cancer compound, for example imatinib. In some embodiments, the method includes the additional step of co-administering to the patient in need thereof an agent that inhibits glucose uptake or inhibits glycolysis.

In some embodiments, the patient is suffering from at least one tumor caused by the cancer.

In one aspect, the invention features a method of promoting apoptosis of a p53 deficient cell comprising the step of contacting the cell with phenformin. In some embodiments, the method includes the additional step of assaying the cell for p53 deficiency (e.g., prior to the administration of phenformin). In some embodiments, the cell is assayed for a p53 mutation, for example, by direct DNA sequencing or Immunohistochemistry (IHC). In some embodiments, the method includes the additional step of contacting the cell with an agent that inhibits glucose uptake or inhibits glycolysis. In some embodiments, the method includes the additional step of assaying the cell for unwanted expression of c-myc (e.g., prior to the administration of phenformin). In some embodiments, the method includes the additional step of assaying the cell for unwanted consumption of oxygen or unwanted levels of ATP (e.g., prior to the administration of phenformin). In some embodiments, the method includes the additional step of assaying the cell for unwanted mitochondrial electron transport activity (e.g., prior to the administration of phenformin). In some embodiments, the method includes the additional step of assaying the cell for unwanted glutamine metabolism (e.g., prior to the administration of phenformin). In some embodiments, the method includes the additional step of assaying the cell for Bax or Bak deficiency (e.g., prior to the administration of phenformin).

In one aspect, the invention features a method of inhibiting autophagy in a cancer cell comprising the step of contacting the cancer cell with phenformin. In some embodiments, the method includes the additional step of assaying the cancer cell for p53 deficiency prior to the administration of phenformin. In some embodiments, the cancer cell is assayed for a p53 mutation, for example, by direct DNA sequencing or Immunohistochemistry (IHC). In some embodiments, the method includes the additional step of assaying the cell for unwanted expression of c-myc (e.g., prior to the administration of phenformin). In some embodiments, the method includes the additional step of assaying the cell for unwanted consumption of oxygen or unwanted levels of ATP (e.g., prior to the administration of phenformin). In some embodiments, the method includes the additional step of assaying the cell for unwanted mitochondrial electron transport activity (e.g., prior to the administration of phenformin). In some embodiments, the method includes the additional step of assaying the cell for unwanted glutamine metabolism (e.g., prior to the administration of phenformin). In some embodiments, the method includes the additional step of assaying the cell for Bax or Bak deficiency (e.g., prior to the administration of phenformin).

In one aspect, the invention features a method of increasing the efficacy of a chemotherapy agent administered to a patient suffering from cancer, comprising the step of co-administering to the patient a pharmaceutical composition comprising phenformin and a pharmaceutically acceptable carrier.

In some embodiments, the method includes the additional step of co-administering to the patient an agent that inhibits glucose uptake or inhibits glycolysis.

In some embodiments, the methods comprise the additional step of assaying the cancer for p53 deficiency prior to the administration of phenformin. In some embodiments, the cancer is assayed for a p53 mutation, for example, by direct DNA sequencing or Immunohistochemistry (IHC). In some embodiments, the method includes the additional step of assaying the cell for unwanted expression of c-myc (e.g., prior to the administration of phenformin). In some embodiments, the method includes the additional step of assaying the cell for unwanted consumption of oxygen or unwanted levels of ATP (e.g., prior to the administration of phenformin). In some embodiments, the method includes the additional step of assaying the cell for unwanted mitochondrial electron transport activity (e.g., prior to the administration of phenformin). In some embodiments, the method includes the additional step of assaying the cell for unwanted glutamine metabolism (e.g., prior to the administration of phenformin). In some embodiments, the method includes the additional step of assaying the cell for Bax or Bak deficiency (e.g., prior to the administration of phenformin).

In one aspect, the invention features a pharmaceutical composition comprising: phenformin; an anti-cancer agent; and a pharmaceutically acceptable carrier.

In some embodiments, the second anti-cancer agent is selected from a chemotherapy agent, a targeted cancer compound, an agent that inhibits glucose uptake and an agent that inhibits glycolysis.

In one aspect, the invention features a kit comprising: a first vessel containing a pharmaceutically components for assaying a cancer for a 53 deficiency; a second vessel containing a pharmaceutically acceptable composition comprising phenformin and a pharmaceutically acceptable carrier; and instructions for using said kit to perform an assay to determine whether a cancer is deficient in p53, and if the cancer is deficient in p53 instructions to administer to a subject having the cancer deficient in p53 phenformin.

In one aspect, the invention features a method of selecting a patient for treatment, e.g., a patient suffering from a cancer characterized by cells that are deficient in p53, comprising: selecting a patient on the basis of the patient having cancer cells that are deficient in p53; optionally, selecting a drug, e.g., phenformin, e.g., on the basis that the drug is useful for treating p53 deficient cancer; and optionally, administering to the patient in need thereof a pharmaceutical composition comprising phenformin and a pharmaceutically acceptable carrier.

In one aspect, the invention features a method of selecting a drug for treating a patient suffering from a cancer characterized by cells that are deficient in p53, comprising: optionally, selecting a drug, e.g., phenformin, e.g., on the basis that the drug is useful for treating p53 deficient cancer; and optionally, administering to the patient in need thereof a pharmaceutical composition comprising phenformin and a pharmaceutically acceptable carrier.

In one aspect, the invention features a method of selecting a patient for treatment, e.g., a patient suffering from a cancer, and selecting a drug for treating said patient comprising: selecting a patient on the basis of the patient having cancer cells that are deficient in p53; selecting a drug, e.g., phenformin, e.g., on the basis that the drug is useful for treating p53 deficient cancer; and optionally, administering to the patient in need thereof a pharmaceutical composition comprising phenformin and a pharmaceutically acceptable carrier.

In one aspect, the invention features a method of treating a patient suffering from a cancer characterized by cells that are characterized by unwanted, e.g., increased over wildtype, c-myc expression, comprising the step of administering to the patient in need thereof a therapeutically effective amount of a biguanide, e.g., phenformin or metformin.

In some embodiments, the method includes the additional step of determining if the cancer has unwanted c-myc expression, e.g., by assaying the cancer for unwanted c-myc expression prior to the administration of the biguanide. In some embodiments, the method includes the additional step of evaluating the patient for a mutation that alters c-myc expression, for example, by direct DNA sequencing or Immunohistochemistry (IHC).

In some embodiments, the cancer is selected from colon cancer or leukemia.

In some embodiments, the cancer is characterized by cells that are deficient in p53. In some embodiments, the cancer is characterized by unwanted consumption of oxygen or unwanted levels of ATP. In some embodiments, the cancer is characterized by unwanted mitochondrial electron transport activity. In some embodiments, the cancer is characterized by unwanted glutamine metabolism. In some embodiments, the cancer is characterized by Bax or Bak deficiency. In some embodiments, the cancer is selected from colon cancer or leukemia.

In some embodiments, the method includes the additional step of subjecting the patient in need thereof to a second anti-cancer therapeutic treatment selected from radiation therapy, chemotherapy or treatment with a targeted cancer compound, for example imatinib. In some embodiments, the additional step of co-administering to the patient in need thereof an agent that inhibits glucose uptake or inhibits glycolysis.

In some embodiments, the patient is suffering from at least one tumor caused by the cancer. In some embodiments, the method includes the additional step of assaying the cancer for a deficiency in p53 (e.g., prior to the administration of the biguanide). In some embodiments, the method includes the additional step of assaying the cancer for unwanted consumption of oxygen or unwanted levels of ATP (e.g., prior to the administration of the biguanide). In some embodiments, the method includes the additional step of assaying the cancer for unwanted mitochondrial electron transport activity (e.g., prior to the administration of the biguanide). In some embodiments, the method includes the additional step of assaying the cancer for unwanted glutamine metabolism (e.g., prior to the administration of the biguanide). In some embodiments, the method includes the additional step of assaying the cancer for Bax or Bak deficiency (e.g., prior to the administration of the biguanide). In some embodiments, the method includes the additional step of evaluating the patient for a mutation that is associated with unwanted c-myc expression, for example, by direct DNA sequencing or Immunohistochemistry (IHC) (e.g., prior to the administration of the biguanide).

In some embodiments, the cancer is selected from colon cancer or leukemia.

In some embodiments, the method includes the additional step of subjecting the patient in need thereof to a second anti-cancer therapeutic treatment selected from radiation therapy, chemotherapy or treatment with a targeted cancer compound, for example, imatinub. In some embodiments, the method includes the additional step of co-administering to the patient in need thereof an agent that inhibits glucose uptake or inhibits glycolysis.

In some embodiments, the patient is suffering from at least one tumor caused by the cancer.

In one aspect, the invention features a method of promoting apoptosis of a cell having unwanted expression of c-myc comprising the step of contacting the cell with a biguanide, e.g., phenformin or metformin.

In some embodiments, the method includes the additional step of assaying the cell for unwanted expression of c-myc (e.g., prior to the administration of a biguanide). In some embodiments, the cell is assayed for unwanted expression of c-myc, for example, by direct DNA sequencing or Immunohistochemistry (IHC). In some embodiments, the method includes the additional step of contacting the cell with an agent that inhibits glucose uptake or inhibits glycolysis.

In some embodiments, the cell is deficient in p53.

In some embodiments, the method includes the additional step of assaying the cell for p53 deficiency (e.g., prior to the administration of the biguanide). In some embodiments, the cell is assayed for a p53 mutation, for example, by direct DNA sequencing or Immunohistochemistry (IHC) (e.g., prior to the administration of the biguanide). In some embodiments, the method includes the additional step of assaying the cancer for unwanted consumption of oxygen or unwanted levels of ATP (e.g., prior to the administration of the biguanide). In some embodiments, the method includes the additional step of assaying the cancer for unwanted mitochondrial electron transport activity (e.g., prior to the administration of the biguanide). In some embodiments, the method includes the additional step of assaying the cancer for unwanted glutamine metabolism (e.g., prior to the administration of the biguanide).

In one aspect, the invention features a kit comprising: a first vessel containing a pharmaceutically components for assaying a cancer for c-myc overexpression; a second vessel containing a biguanide, e.g., phenformin or metformin; and instructions for using said kit to perform an assay to determine whether a cancer has c-myc overexpression, and if so, instructions to administer to a subject having the cancer with c-myc overexpression, a biguanide, e.g., phenformin or metformin.

In one aspect, the invention features a method of selecting a patient for treatment, e.g., a patient suffering from a cancer characterized by cells that have unwanted c-myc expression, comprising: selecting a patient on the basis of the patient having cancer cells that have unwanted c-myc expression; optionally, selecting a drug, e.g., a biguanide, e.g., phenformin or metformin, e.g., on the basis that the drug is useful for treating cancer having unwanted c-myc expression; and optionally, administering to the patient in need thereof a therapeutically effective amount of a biguanide, e.g, phenformin or metformin.

In one aspect, the invention features a method of selecting a drug for treating a patient suffering from a cancer characterized by cells that have unwanted c-myc expression, comprising: optionally, selecting a drug, e.g., a biguanide, e.g., phenformin or metformin, e.g., on the basis that the drug is useful for treating a cancer have unwanted c-myc expression; and optionally, administering to the patient in need thereof a therapeutically effective amount of a biguanide, phenformin or metformin.

In one aspect, the invention features a method of selecting a patient for treatment, e.g., a patient suffering from a cancer characterized by cells that have unwanted c-myc expression, and selecting a drug for treating said patient comprising: selecting a patient on the basis of the patient having cancer cells that have unwanted c-myc expression; selecting a drug, e.g., a biguanide, e.g., phenformin or metformin, e.g., on the basis that the drug is useful for treating cancer having unwanted c-myc expression; and optionally, administering to the patient in need thereof a therapeutically effective amount of a biguanide, e.g, phenformin or metformin. In one aspect, the invention features a method of treating a patient suffering from a cancer characterized by having one or more characteristics described herein, e.g., a cancer characterized as having unwanted mitochondrial electron transport chain activity (e.g., a cancer having unwanted oxygen consumption or unwanted ATP levels), a cancer having unimpaired glutamine metabolism, or a cancer having Bax or Bak deficiency, comprising the step of administering to the patient in need thereof a therapeutically effective amount of a biguanide, e.g., phenformin or metformin.

In some embodiments, the method includes the additional step of determining if the cancer has unwanted mitochondrial electron transport chain activity (e.g., a cancer having unwanted oxygen consumption or unwanted ATP levels), unimpaired glutamine metabolism, or a Bax or Bak deficiency, e.g., by assaying the cancer prior to the administration of the biguanide.

In some embodiments, the cancer is selected from colon cancer or leukemia.

In some embodiments, the method includes determining if the cancer is characterized by cells that are deficient in p53 (e.g., prior to the administration of the biguanide).

In some embodiments, the method includes the additional step of assaying the cell for p53 deficiency (e.g., prior to the administration of the biguanide). In some embodiments, the cell is assayed for a p53 mutation, for example, by direct DNA sequencing or Immunohistochemistry (IHC) (e.g., prior to the administration of the biguanide). In some embodiments, the method includes the additional step of assaying the cell for unwanted expression of c-myc (e.g., prior to the administration of the biguanide). In some embodiments, the cell is assayed for unwanted expression of c-myc, for example, by direct DNA sequencing or Immunohistochemistry (IHC). In some embodiments, the method includes the additional step of assaying the cell for Bax or Bak deficiency (e.g., prior to the administration of the biguanide).

In some embodiments, the method includes the additional step of subjecting the patient in need thereof to a second anti-cancer therapeutic treatment selected from radiation therapy, chemotherapy or treatment with a targeted cancer compound, for example imatinib. In some embodiments, the method includes the additional step of co-administering to the patient in need thereof an agent that inhibits glucose uptake or inhibits glycolysis.

In some embodiments, the patient is suffering from at least one tumor caused by the cancer. In some embodiments, the patient is suffering from at least one tumor caused by the cancer.

In one aspect, the invention features a method of promoting apoptosis of a cell having one or more characteristics described herein, e.g., unwanted mitochondrial electron transport chain activity (e.g., a cancer having unwanted oxygen consumption or unwanted ATP levels), unimpaired glutamine metabolism, or a Bax or Bak deficiency, comprising the step of contacting the cell with a biguanide, e.g., phenformin or metformin.

In some embodiments, the method includes the additional step of assaying the cell for unwanted expression of c-myc (e.g., prior to the administration of the biguanide). In some embodiments, the cell is assayed for unwanted expression of c-myc, for example, by direct DNA sequencing or Immunohistochemistry (IHC). In some embodiments, the cell is deficient in p53. In some embodiments, the method includes the additional step of assaying the cell for p53 deficiency (e.g., prior to the administration of the biguanide). In some embodiments, the cell is assayed for a p53 mutation, for example, by direct DNA sequencing or Immunohistochemistry (IHC). In some embodiments, the method includes the additional step of assaying the cancer for unwanted consumption of oxygen or unwanted levels of ATP (e.g., prior to the administration of the biguanide). In some embodiments, the method includes the additional step of assaying the cancer for unwanted mitochondrial electron transport activity (e.g., prior to the administration of the biguanide). In some embodiments, the method includes the additional step of assaying the cancer for unwanted glutamine metabolism (e.g., prior to the administration of the biguanide). In some embodiments, the method includes the additional step of assaying the cell for Bax or Bak deficiency (e.g., prior to the administration of the biguanide). In some embodiments, the method includes the additional step of contacting the cell with an agent that inhibits glucose uptake or inhibits glycolysis (e.g., prior to the administration of the biguanide).

In one aspect, the invention features a kit comprising:
a first vessel containing a pharmaceutically components for assaying a cancer characterized by having one or more characteristics described herein, e.g., a cancer characterized as having unwanted mitochondrial electron transport chain activity (e.g., a cancer having unwanted oxygen consumption or unwanted ATP levels), a cancer having unimpaired glutamine metabolism, or a cancer having Bax or Bak deficiency;
a second vessel containing a biguanide, e.g., phenformin or metformin; and instructions for using said kit to perform an assay to determine whether a cancer characterized by having one or more characteristics described herein, e.g., a cancer characterized as having unwanted mitochondrial electron transport chain activity (e.g., a cancer having unwanted oxygen consumption or unwanted ATP levels), a cancer having unimpaired glutamine metabolism, or a cancer having Bax or Bak deficiency, and if so, instructions to administer to a subject having the cancer, a biguanide, e.g., phenformin or metformin.

In one aspect, the invention features a method of selecting a patient for treatment, e.g., a patient suffering from a cancer having one or more characteristics described herein, e.g.,
a cancer characterized as having unwanted Mitochondrial electron transport chain activity (e.g., a cancer having unwanted oxygen consumption or unwanted ATP levels),
a cancer having unimpaired glutamine metabolism, or
a cancer having Bax or Bak deficiency, comprising:
selecting a patient on the basis of the patient having a cancer with one or more of said characteristics, e.g., a cancer characterized as having unwanted mitochondrial electron transport chain activity, unimpaired glutamine metabolism, or a cancer having Bax or Bak deficiency;
optionally, selecting a drug, e.g., a biguanide, e.g., phenformin or metformin, e.g., on the basis that the drug is useful for treating cancer having one or more of said characteristics described herein, e.g., a cancer characterized as having unwanted mitochondrial electron transport chain activity, unimpaired glutamine metabolism, or a cancer having Bax or Bak deficiency; and
optionally, administering to the patient in need thereof a therapeutically effective amount of a biguanide, e.g., phenformin or metformin.

In one aspect, the invention features a method of selecting a drug for treating a patient suffering from a cancer characterized by having one or more characteristics described herein, e.g.,
a cancer characterized as having unwanted mitochondrial electron transport chain activity (e.g., a cancer having unwanted oxygen consumption or unwanted ATP levels),
a cancer having unimpaired glutamine metabolism, or
a cancer having Bax or Bak deficiency, comprising:
optionally, selecting a drug, e.g., a biguanide, e.g., phenformin or metformin, e.g., on the basis that the drug is useful for treating a cancer have having one or more characteristics described herein; and
optionally, administering to the patient in need thereof a therapeutically effective amount of a biguanide, e.g, phenformin or metformin.

In one aspect, the invention features a method of selecting a patient for treatment, e.g., a patient suffering from a cancer characterized by cells having one or more characteristics described herein, e.g., a cancer characterized as having unwanted mitochondrial electron transport chain activity (e.g., a cancer having unwanted oxygen consumption or unwanted ATP levels), a cancer having unimpaired glutamine metabolism, or a cancer having Bax or Bak deficiency, and selecting a drug for treating said patient comprising:

selecting a patient on the basis of the patient having cancer cells having one or more characteristics described herein;

selecting a drug, e.g., a biguanide, e.g., phenformin or metformin, e.g., on the basis that the drug is useful for treating cancer having one or more characteristics described herein; a cancer characterized as having unwanted mitochondrial electron transport chain activity (e.g., a cancer having unwanted oxygen consumption or unwanted ATP levels), a cancer having unimpaired glutamine metabolism, or a cancer having Bax or Bak deficiency; and optionally, administering to the patient in need thereof a therapeutically effective amount of a biguanide, e.g, phenformin or metformin.

The following examples are offered for illustrative purposes and are not intended to limit the invention in any manner. Those of skill in the art will readily recognize a variety of noncritcal parameters which can be changed or modified to yield essentially the same results.

EXAMPLES

Materials and Methods

Cell Lines and Cell Culture:

K562 cell line was obtained from ATCC. Cells were maintained in standard RPMI 1640 media supplemented with 10% Fetal Bovine Serum (FBS) (Gemini), 100 units/ml penicillin, 100 ug/mL streptomycin (Invitrogen), 2 mmol/L glutamine, and 10 mM HEPES buffer. Nutrient restriction experiments were performed using similarly mixed media, using Glutamine-free RPMI 1640 or Glucose-free (Invitrogen) with 10% dialyzed FBS (Gemini). Where indicated, media was supplemented with 4 mmol/L glutamine, 20 mmol/L sodium pyruvate (Sigma), and/or 1 mmol/L ammonium chloride (Sigma). Cell concentration and cell size were assessed with a Coulter Z2 particle analyzer. Cell viability was assessed by the exclusion of 10 ug/mL propidium iodide (Invitrogen), as determined by LSR flow cytometer. Inhibitor experiments were performed using 1 mM phenformin (Sigma), 750 nM imatinib (A generous gift of David Tuveson), and 25 nM rapamycin (Calbiochem).

Western Blot Analysis. Cells were lysed in radioimmunoprecipitation (RIPA) buffer containing protease inhibitors (Complete Mini, Roche Applied Science), and protease inihibitors cocktails I and II (Sigma). BCA Protein Assay kit (Pierce Biotechnology) was used to assess and standardize protein concentrations. Proteins were resolved using a 4-12% NuPage Bis-Tris polyacrylamide gels (Invitrogen), and transferred to nitrocellulose membranes. Membranes were blocked using 5% nonfat dry skim milk and 0.1% Tween. Blots were subsequently probed with primary antibodies against: REDD-1 (Proteintech Group Inc), phospho-ser235/236 S6RP, total S6RP, phospho-thr172 AMPK, total-AMPK, phospho-tyr694/699 STAT5 (Upstate Biotechnology), total STAT5 (Upstate Biotechnology), phospho-thr202/tyr204 p42/44MAPK, total p42/44 MAPK, c-myc (Santa Cruz Biotechnologies), HIF-1a (Biosciences Pharmingen), and tubulin (Sigma). Unless otherwise indicated, all antibodies were obtained from Cell Signaling Technologies. Bands were subsequently detected using horseradish-peroxidase conjugated anti-mouse or anti-rabbit secondary antibodies (GE Healthcare Industries) and enhanced chemiluminescence detection kit (Amersham).

Determination of Oxygen Consumption Rates and ATP Levels.

Oxygen consumption by whole cells was measured as previously described. See Schumacker P T, Chandei N, Agusti A G. Oxygen conformance of cellular respiration in hepatocytes. Am J. Physiol. 1993; 265:L395-402. Briefly, inhibitor-treated (24 hours) K562 cells were resuspended at a concentration of 4 million cells/ml, and 1.4 mL of culture was transferred to a water-jacketed, airtight 3 ml chamber with a Clarke oxygen electrode, (Hansatech Instruments). Electron transport activity was manipulated through mitochondrial uncoupling with 10 uL of 1 mM Carbonyl cyanide 3-chlorophenylhydrazone (CCCP) (Sigma), and media supplementation of sodium Succinate (25 uL of 1M stock), after membrane permeabilization with digoxin (4 ul of 25 mg/ml stock). Relative ATP levels were assessed using the Invitrogen ATP determination kit (A22066), as per protocol, using 25,000 cell pellets. Cells were assayed after 24 hours of inhibitor treatment, as indicated, and results were expressed as Arbitrary Units/25000 cells.

Determination of Glucose and Glutamine Consumption.

Daily cell culture supernatants were collected, and analyzed using the Nova Biomedical Bioprofile Flex Analyzer, which determined glucose, glutamine, lactate, and ammonia levels. For the HIF-1 induction experiments, K562 cells were incubated at 4 million cells/ml in a plastic tube (Falcon 35-2059) with rubber stopper (Kontes Glass Company #882310), with constant stirring at 37 C. At indicated time points, tubes were spun to pellet cells, and the glucose, lactate and pO2 content of supernatant was assessed by syringe sampling through an air-tight rubber stopper. After supernatant sampling, cells were collected and lysates were prepared as described above.

Example 1

Phenformin Inhibits Cell Growth of p53-Deficient Erythroleukemia Cell Line (K562 Cells)

K562 cells were treated with a single dose of imatinib, rapamycin, or phenformin, and assessed for cell number (Coulter Counter) and cell viability (by propidium iodide exclusion) over four days. While both phenformin and imatinib halted K562 proliferation, phenformin-treated cells exhibited the earlier growth arrest, as no increase in cell number was observed after the first 24 hours (FIG. 1A). Imatinib-treated cells ceased proliferation after 2 days, after approximately one doubling of cell number had been achieved. Rapamycin, in contrast, had only a mild effect on K562 proliferation.

Figure 1B:
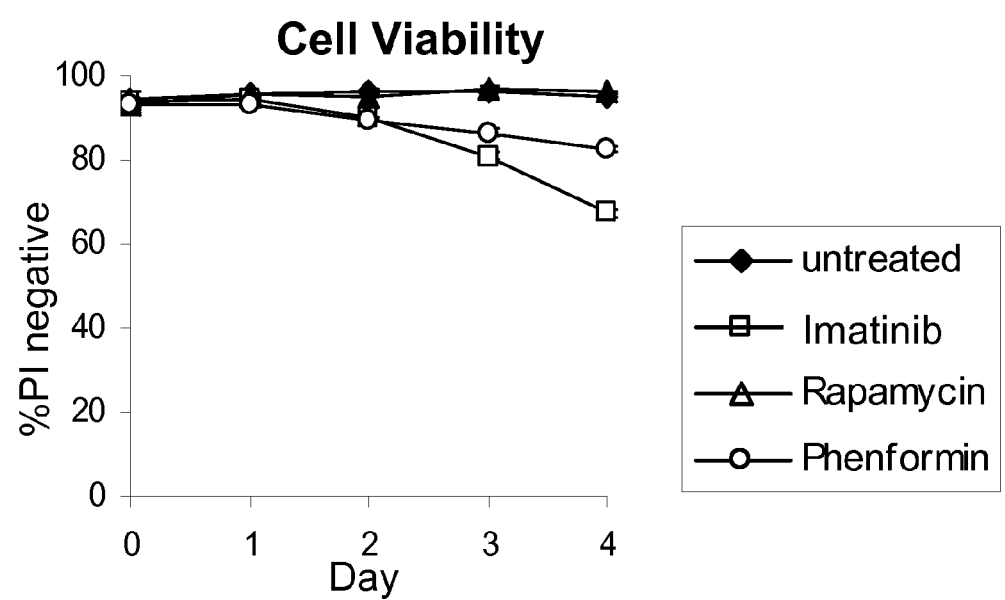
FIG. 1B depicts the effect of imatinib, rapamycin, and phenformin on the viability of chronic myelogenous leukemia (CML) cells (K562 cells).

Imatinib treatment also induced a decrease in viability (FIG. 1B), consistent with reports of imatinib-induced apoptosis in K562 cells. Phenformin treatment was associated with greater viability over the four days, indicating a distinct mechanism of growth arrest in these cells. Rapamycin-treated cell viability was indistinguishable from untreated control cells.

Example 2

Phenformin Inhibits STAT Activation in K562 Cells

Figure 2:
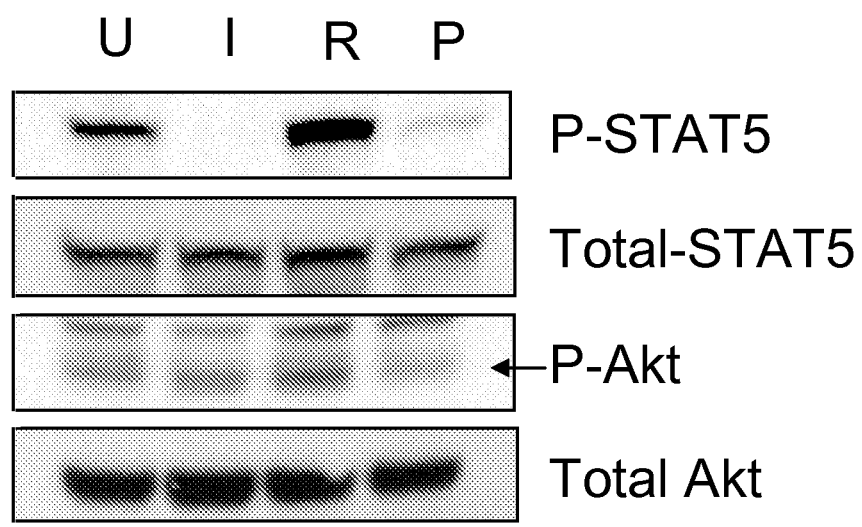
FIG. 2 depicts the effect of imatinib (I), rapamycin (R), and phenformin on STAT activation. Untreated sample represented by (U).

To characterize the pattern of signaling pathway activation in inhibitor-treated cells, the activity of the Akt and Jak-STAT pathways were examined, two pathways known to be activated by the bcr-abl oncogenic signaling. Proteins were isolated from cells, 24 hours after inhibitor treatment, and assessed for levels of phospho-Akt (Thr 173) and phospho-STAT5 (tyr694/699), as well as total levels of these proteins as loading controls. Imatinib (I) treatment decreased the levels of STAT5 phosphorylation, but left Akt phosphoylation intact. Phenformin (P) induced a similar pattern of Jak-STAT inhibition, with no suppression of Akt phosphorylation. Rapamycin (R) treated cells, in contrast, appeared to have elevated levels of both phospho-STAT5 and phospho-Akt, relative to untreated (U) control cells. These results are depicted in FIG. 2.

Example 3

Phenformin Inhibits Cell Proliferation Better than Metformin

Figure 3:
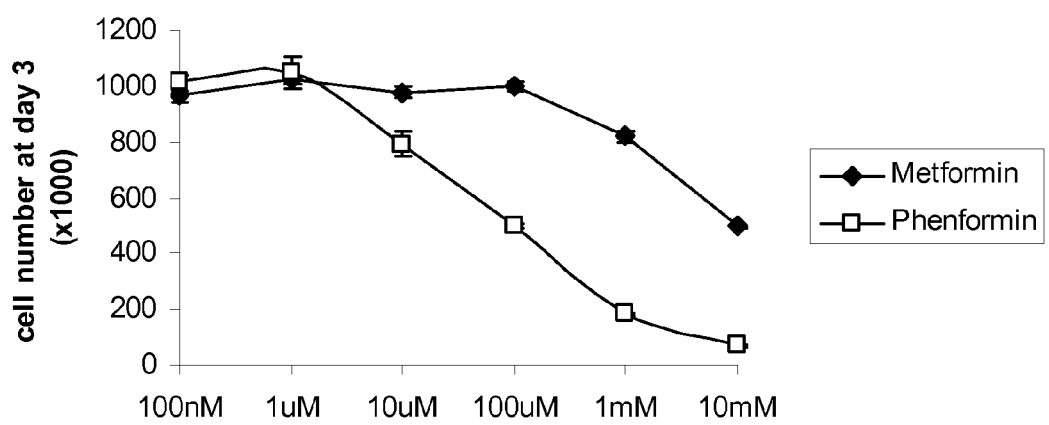
FIG. 3 depicts the comparison of the effects of phenformin and metformin on cell proliferation.

Despite its reported ability to inhibit cancer growth in vivo, metformin was found to be a relatively weak inhibitor of K562 proliferation. In contrast, phenformin was found to be a more potent inhibitor of K562 proliferation. Direct comparison of metformin and phenformin activity, over a range of biguanide concentrations, was accomplished by comparing total K562 cell number after three days of exposure to a single dose of phenformin or metformin, as indicated (FIG. 3). Cell cultures were started at a density of 200,000 cells/ml. These results demonstrate that phenformin was 100-fold more potent than metformin in inhibiting K562 proliferation.

Example 4

Figure 4:
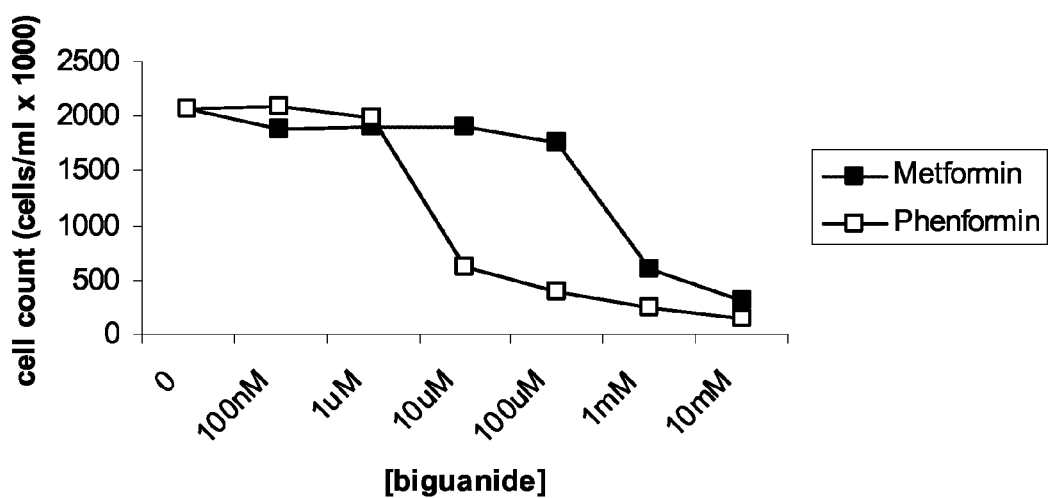
FIG. 4 depicts the comparison of the effects of phenformin and metformin on cell proliferation of p53-deficient cell lines having Bax- and Bak-deficiency.

Phenformin Inhibits Cell Proliferation in p53-Deficient Cells Having Bax- and Bak-Deficiency The ability of phenformin to inhibit the proliferation of Bax-Bak deficient lymphocytes, in the presence of IL-3 stimulation, was assessed, and compared to the activity of metformin. Direct comparison of metformin and phenformin activity, over a range of biguanide concentrations, was accomplished by comparing total cell numbers of bax-bak deficient cells after three days exposure to a single dose of phenformin or metformin, as indicated (FIG. 4). Cell cultures were started at a density of 200,000 cells/ml. These results demonstrate that phenformin prevents proliferation of bax-bak deficient cells, and that phenformin is consistently more potent an inhibitor than metformin.

Example 5

Phenformin's Effect on Aerobic Glycolysis

To investigate the metabolic effects of phenformin on K562 cells, we compared the glycolytic activity of the cells in the drug-treated cultures by quantifying total glucose consumption and lactate production over four days (FIGS. 5A and 5B, respectively), by collecting and analyzing daily cell culture supernatants using a Nova Biomedical Bioprofile Flex Analyzer. Imatinib-treated cells exhibited minimal glucose consumption and lactate production, indicating a loss of aerobic glycolysis. Rapamycin-treated cells accumulated only half the lactate level of untreated cells, a finding in keeping with the proposed role of the TOR pathway in the upregulation of glycolysis. In contrast, phenformin-treated cells accumulated lactate and consumed glucose at rates similar to untreated cells, despite the profound difference in their proliferative phenotypes (See FIG. 1A). Phenformin was therefore novel in its ability to dissociate aerobic glycolysis from cell proliferation.

Example 6

Phenformin Decreased Oxygen Consumption and ATP Levels

Figure 6A:
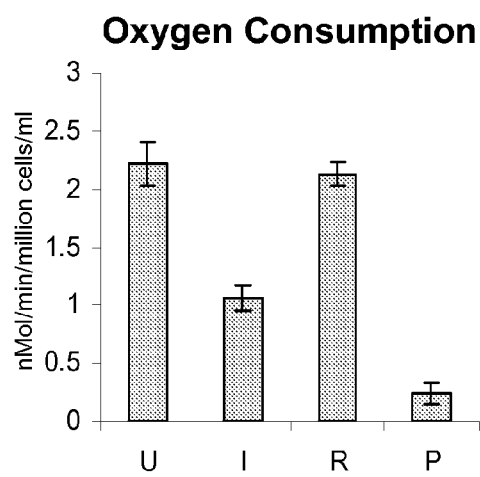
FIG. 6A depicts the effects of imatinib (I), rapamycin (R), and phenformin (P) (versus untreated (U)) on oxygen consumption.

Electron Transport Activity (ETC) activity, as determined by oxygen consumption rates, was assessed after treatment with each inhibitor, using a water-jacketed, airtight 3 ml chamber with a Clarke oxygen electrode, (Hansatech Instruments). Phenformin-treated cells (P) demonstrated the most dramatically reduced oxygen consumption relative to untreated (U) controls (FIG. 6A; I=imatinib, R=rapamycin).

Figure 6B:
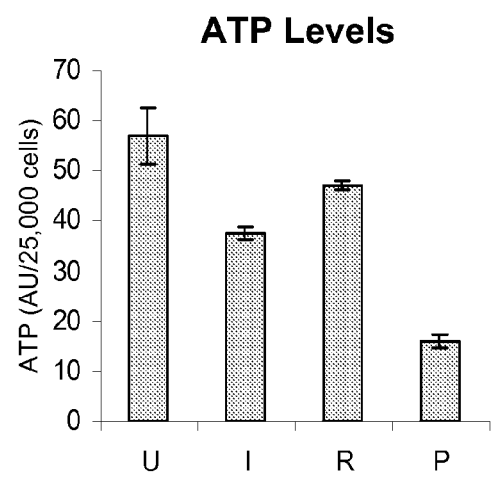
FIG. 6B depicts the effects of imatinib (I), rapamycin (R), and phenformin (P) (versus untreated (U)) on ATP levels.

Despite high levels of glucose consumption by phenformin-treated cells, their intracellular ATP levels were the most profoundly reduced (FIG. 6B) among inhibitor-treated cells, as determined by use of the Invitrogen ATP determination kit (A22066), using 25,000 cell pellets. Cells were assayed after 24 hours of inhibitor treatment, as indicated, and results were expressed as Arbitrary Units/25000 cells. Oxygen consumption correlated closely with relative levels of intracellular ATP.

Example 7

Phenformin-Treated Cells Exhibit Glucose Deprivation Sensitivity

Figure 7A:
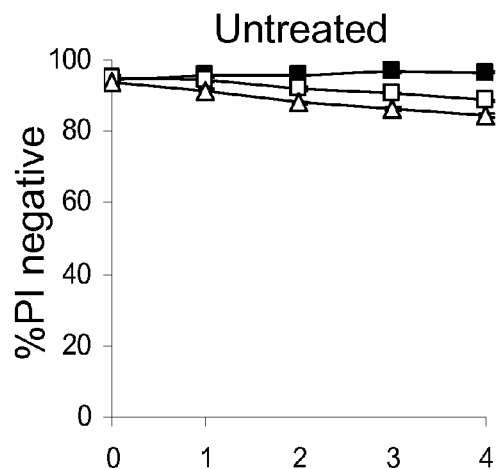
FIGS. 7A, 7B, 7C, and 7D depict the effect of imatinib (FIG. 7B), rapamycin (FIG. 7C), and phenformin (FIG. 7D), versus an untreated sample (FIG. 7A), on glucose and glutamine deprived cells. RPMI is a standard cell culture medium that is not deficient in either glucose or glutamine.
Figure 7B:
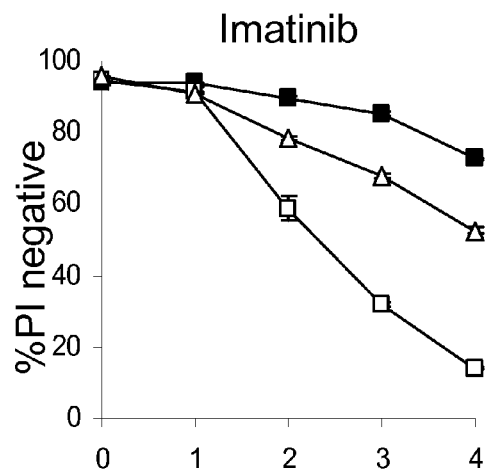
Figure 7C:
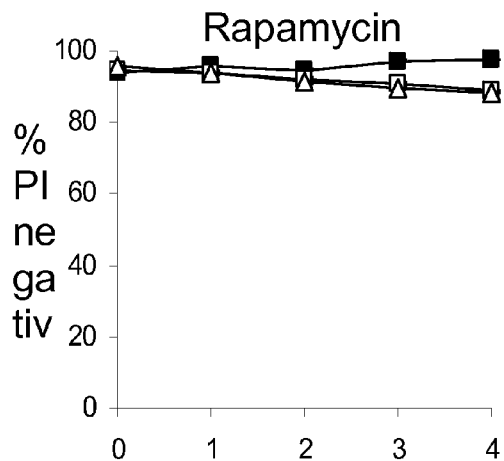
Figure 7D:
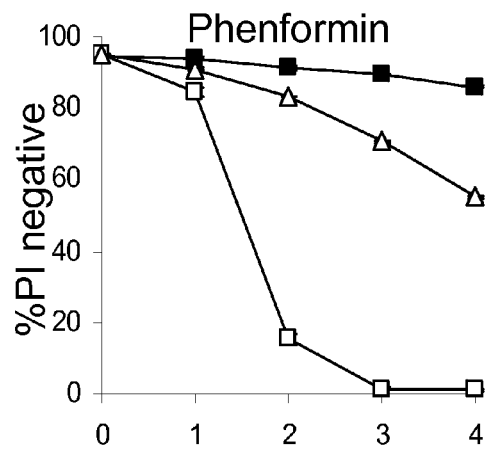

The viability of K562 cells after variable inhibitor treatment, and selective medium depletion of glucose or glutamine, is shown. Cell viability was determined by propidium iodide exclusion of 10,000 cells (via FACS analysis), taken from each culture each day of experiment. As seen in FIG. 7A, untreated K562 control cells show little difference in viability over for 4 days, whether incubated in media depleted of glutamine or glucose, or in complete media. Similarly, rapamycin-treated cells also showed little change in viability under these media conditions (FIG. 7C). Both imatinib and phenformin demonstrate significantly increased cell death upon glutamine depletion, but phenformin treated cells exhibited significantly increased cell death upon glucose depletion, consistent with increased reliance upon glycolysis in phenformin-treated cells (FIGS. 7B and 7D).

Example 8

Phenformin Inhibits Glutamine Metabolism

Figure 8:
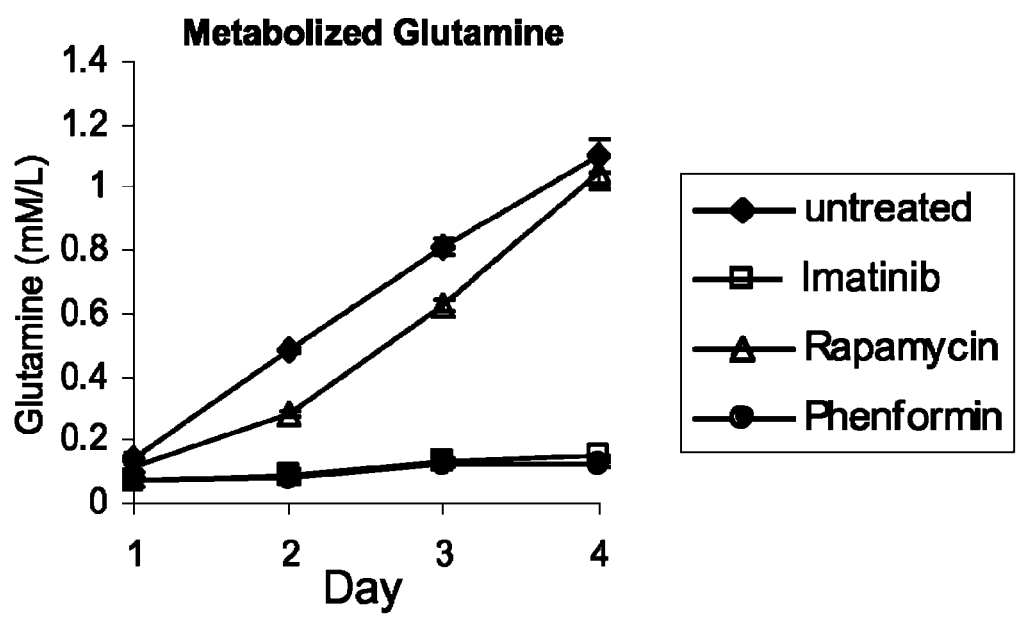
FIG. 8 depicts the effects of imatinib, rapamycin, and phenformin on glutamine metabolism.

To further investigate what functional role the TCA cycle might play in K562 proliferation, we compared the ability of phenformin-treated cells to metabolize glutamine. In tumor cells, glutaminolysis is important in maintaining TCA cycle activity, as it serves to provide an additional source of TCA cycle intermediates (a-ketoglutarate) to the mitochondria. Glutamine uptake was observed only by rapamycin-treated and untreated control cells (FIG. 8). In contrast, both imatinib and phenformin-treated cells failed to demonstrate substantial glutamine uptake over the four days.

Example 9

Phenformin Effect on BCR-Abl-Induced C-Myc Expression in K562 Cells

Figure 9:
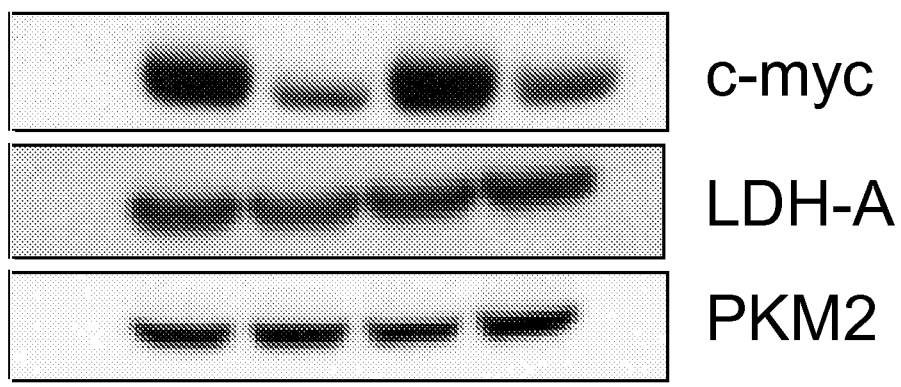
FIG. 9 depicts the effects of (I), rapamycin (R), and phenformin (P) (versus untreated (U)) on BCR-Abl-induced c-myc expression in K562 cells.

Expression levels of c-myc in inhibitor and untreated (U) control K562 cells was investigated by Western Blotting of cellular extracts prepared after 24 hours of inhibitor treatment. As shown in FIG. 9, phenformin (P) inhibited c-myc expression more effectively than rapamycin (R), and was commensurate in efficacy with imatinib (I).

Example 10

Figures 10A, 10B, 10C:
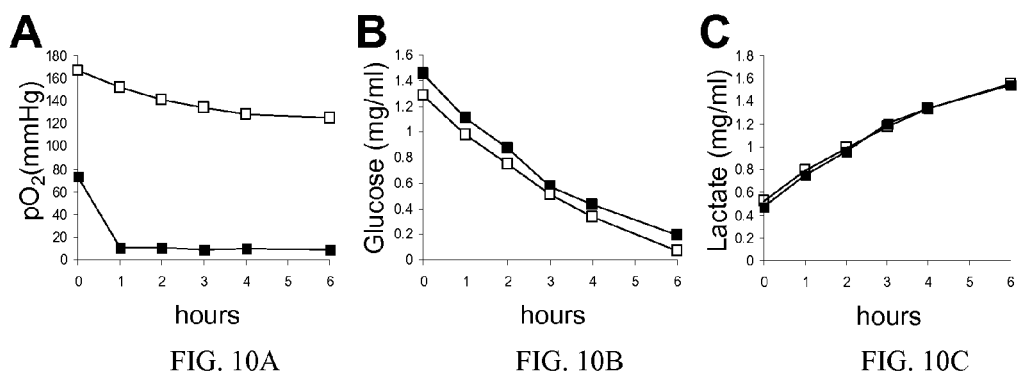
FIG. 10 depicts the partial oxygen pressure (pO2) (A), glucose level (B), and lactate level (C) of phenformin-treated and untreated K562 cells after incubation at 37° C. in airtight tubes.
FIG. 10D depicts a Western blot analysis of phenformin-treated and untreated K562 cells after incubation at 37° C. in airtight tubes, using tubulin as loading control.
Figure 10D:
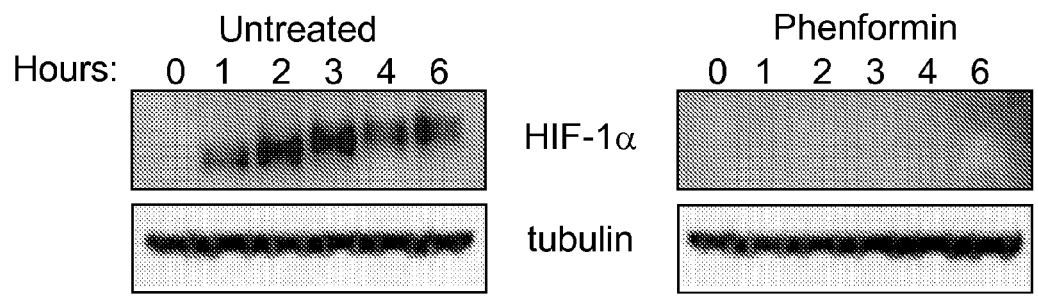

Phenformin Treatment Prevents HIF-1 Expression, by Preventing Establishment of Hypoxia Phenformin-treated and untreated K562 cells were transferred to airtight tubes and incubated at 37° C. for 1 to 6 hours. At one hour intervals, supernatants were analyzed for partial oxygen pressure (pO2), glucose, and lactate levels, while cells were collected for protein extract preparation. Oxygen consumption by untreated K562 cells was sufficiently rapid such that oxygen levels were significantly reduced during the time required for processing of time=0 sample. While phenformin-treated cells exhibited similar rates of glucose consumption (FIG. 10B) and lactate production (FIG. 10C), the two cultures were distinguished by dramatically different partial oxygen pressures (FIG. 10A). The absence of hypoxia in the phenformin-treated culture prevented HIF-1 induction in these cells (FIG. 10D). Western Blot analysis demonstrates HIF-1a induction is limited to untreated cells in hypoxic media. FIG. 10D. Tubulin serves as loading control.

What is claimed is:

1. A method of treating cancer in a patient comprising
   assaying the cancer for at least one of p53 deficiency, over-expression of c-myc, Bax-deficiency, Bak-deficiency, and glutamine dependence; and
   in response to a positive assay for at least one of p53 deficiency, over-expression of c-myc, Bax-deficiency, Bak deficiency, and glutamine dependence,
   administering to the patient a therapeutically effective amount of phenformin.

2. The method of claim 1, wherein the cancer is assayed by direct DNA sequencing or immunohistochemistry.

3. The method of claim 1, wherein the assay is positive for p53 deficiency.

4. The method of claim 1, wherein the assay is positive for over-expression of c-myc.

5. The method of claim 1, wherein the assay is positive for Bax-deficiency.

6. The method of claim 1, wherein the assay is positive for Bak-deficiency.

7. The method of claim 1, wherein the assay is positive for glutamine dependence.

8. The method of claim 1, wherein the cancer comprises chronic myelogenous leukemia.

9. The method of claim 1, further comprising administering at least one additional cancer treatment.

10. The method of claim 9, wherein the cancer treatment comprises a chemotherapy agent, radiation, hormone, immunotherapeutic agent, targeted cancer compound, a glycolysis inhibition agent, or a glucose uptake inhibition agent.

11. A method for adjusting the chemotherapeutical treatment of a neoplasm in a patient comprising
    assaying the neoplasm for at least one of p53 deficiency, over-expression of c-myc, Bax-deficiency, Bak-deficiency, and glutamine dependence; and
    in response to a positive assay for at least one of p53 deficiency, over-expression of c-myc, Bax-deficiency, Bak deficiency, and glutamine dependence
    administering to the patient a therapeutically effective amount of phenformin; and
    in response to a negative assay for at least one of p53 deficiency, over-expression of c-myc, Bax-deficiency, Bak-deficiency, and glutamine dependence, refraining from administering to the patient a therapeutically effective amount of phenformin.

12. The method of claim 1, comprising assaying the cancer for p53 deficiency and in response to a positive assay p53 deficiency, administering to the patient a therapeutically effective amount of phenformin.

13. The method of claim 1, comprising assaying the cancer for glutamine dependence and in response to a positive assay for glutamine dependence, administering to the patient a therapeutically effective amount of phenformin.

14. The method of claim 1, comprising assaying the cancer for over-expression of c-myc and in response to a positive assay for over-expression of c-myc, administering to the patient a therapeutically effective amount of phenformin.

15. The method of claim 1, comprising assaying the cancer for Bax-deficiency and in response to a positive assay for Bax-deficiency, administering to the patient a therapeutically effective amount of phenformin.

16. The method of claim 1, comprising assaying the cancer for Bak-deficiency and in response to a positive assay for Bak-deficiency, administering to the patient a therapeutically effective amount of phenformin.

* * * * *

UNITED STATES PATENT AND TRADEMARK OFFICE
CERTIFICATE OF CORRECTION

PATENT NO.       : 8,574,829 B2                                                                 Page 1 of 1
APPLICATION NO.  : 13/260838
DATED            : November 5, 2013
INVENTOR(S)      : Thompson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this
Twenty-second Day of September, 2015

Michelle K. Lee
*Director of the United States Patent and Trademark Office*